United States Patent
Faour

Patent Number: 6,136,020
Date of Patent: Oct. 24, 2000

[54] TREATMENT FOR PROSTATITIS AND APPARATUS THEREFOR

[76] Inventor: Ali M. Faour, 23412 Al Wahda Street Dafco Build., Sharjah, United Arab Emirates

[21] Appl. No.: 09/105,138

[22] Filed: Jun. 26, 1998

[51] Int. Cl.$^7$ .................................................. A61B 17/36
[52] U.S. Cl. .............................. 607/96; 607/101; 607/116
[58] Field of Search ............................ 607/96, 101–102, 607/113, 138, 115, 116

[56] References Cited

U.S. PATENT DOCUMENTS

| | | | |
|---|---|---|---|
| 5,354,325 | 10/1994 | Chive et al. | 607/101 |
| 5,370,675 | 12/1994 | Edwards et al. | 607/101 |
| 5,404,881 | 4/1995 | Cathaud et al. | |
| 5,480,417 | 1/1996 | Hascoet et al. | 607/101 |
| 5,540,655 | 7/1996 | Edwards et al. | 604/22 |
| 5,857,997 | 1/1999 | Cimino et al. | 604/95 |

Primary Examiner—Linda C. M. Dvorak
Assistant Examiner—Roy Gibson

[57] ABSTRACT

A method and apparatus for treating prostatitis is provided. The apparatus includes two probes, a control unit, and a monitor. A urethral probe selectively applies low frequency pulses to the prostate region as well as infrared heating. A rectal probe applies microwave heating to the prostate region and also includes an ultrasound element for generating an image of the prostate to facilitate diagnosis and treatment of the patient.

6 Claims, 5 Drawing Sheets

TREATMENT FOR PROSTATITIS AND APPARATUS THEREFOR

BACKGROUND OF THE INVENTION

1. Field of the Invention

The present invention relates to methods for treating prostatitis. More specifically, it relates to an improved method and apparatus for applying thermal and microwave energy, as well as electro-stimulation to the prostate region to effect treatment of prostatitis. Ultrasound is used for diagnostic purposes.

2. Background of the Invention

Various treatments for prostatitis and other prostate problems have been developed over the years, and have ranged from various surgical procedures to medication. One of the newest procedures involves the use of heat or thermal therapy, and several devices for applying heat to the prostate tissues have been developed, with varying levels of success.

U.S. Pat. No. 5,733,315 discloses the use of ultrasound to apply thermal energy to the prostate tissues. The ultrasound element has a plurality of regions which are deactivated to reduce the amount of heat applied to the rectal wall of the patient. In contrast, the present invention has several elements for applying heat to the prostate tissues, and the elements are controlled to selectively apply heat to various portions of the prostate tissues without applying excessive heat to the rectal wall or other non-affected areas.

U.S. Pat. No. 5,620,480 also discloses a device for applying thermal therapy to the prostate tissues. A coolant is circulated within the device in order to reduce damage to the surrounding non-affected areas. The present invention contemplates controlling application of thermal energy by having an array of heating elements which are electronically activated to selectively apply heat to the prostate tissues without damaging adjacent non-affected areas.

SUMMARY OF THE INVENTION

Briefly, the invention contemplates a method and apparatus for treating prostatitis. The apparatus comprises two probes, a control unit, and a monitor. A urethral probe has electrodes which selectively apply low frequency pulses to the prostate region as well as resistive heating. A rectal probe applies microwave heating to the prostate region and also includes an ultrasound element for generating an image of the prostate to facilitate diagnosis and treatment of the patient.

Accordingly, it is a principal object of the invention to provide a new and improved treatment for prostatitis.

It is a major object of this invention to provide an apparatus for treatment of prostatitis.

It is another object of the invention to provide such an apparatus which selectively applies heat to prostate tissues.

It is another object of the invention to provide a treatment for prostatitis which will decrease the size of the inflamed prostate gland.

It is another object of the invention to provide such an apparatus which has an array of elements for applying thermal energy to the prostate tissues.

It is another object of the invention to provide an apparatus for the treatment of prostatitis which applies alternate electro-stimulation to contract the fibrous muscles of the prostate to remove the inflammatory product of the prostate gland.

These and other objects of the present invention will become readily apparent upon further review of the following specification and drawings.

DETAILED DESCRIPTION OF THE PREFERRED EMBODIMENTS

Figure 1:
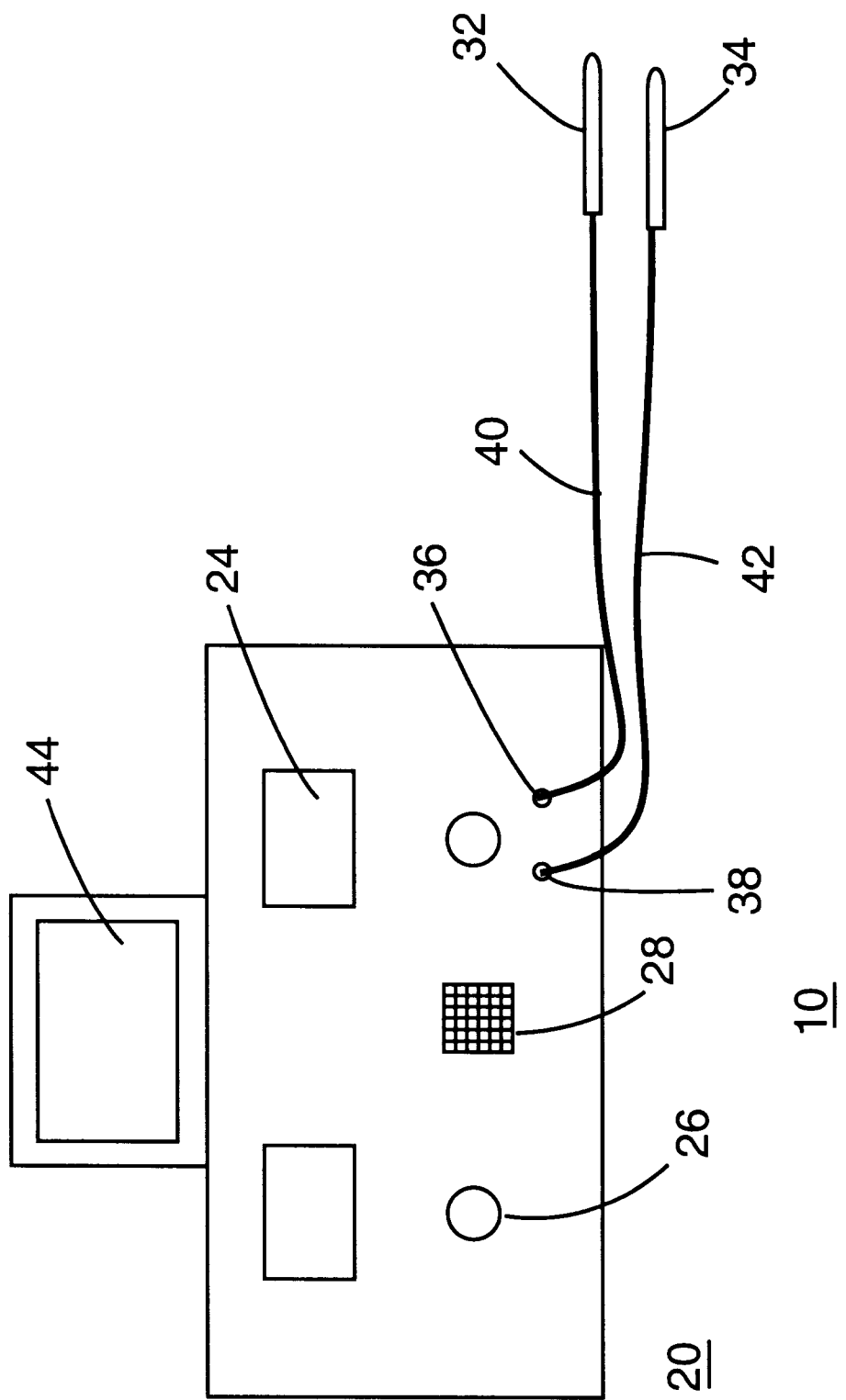
FIG. 1 is a perspective view of the components of the present invention.

Referring now to FIGS. 1–6 the system of the present invention, generally indicated by the numeral 10, is shown. The invention 10 includes a control system 20 contained within a housing 22, the housing 22 including display 24 and adjustment 26 means. The display means 24 may be an LED display and the adjustment means 26 may be a pair of rotatable knobs functionally connected to potentiometers as will be discussed later. A speaker 28 or other acoustic transducer may be contained within the housing to provide audible feedback to the operator during the treatment. A urethral probe 32 and a rectal probe 34 are connected to the housing 22 via terminals 36, 38 which provide for the appropriate electrical connections to the probes 32, 34 via cables 40, 42 as will be explained later. The urethral probe 32 has three conductive rings for applying low frequency energy and infrared heat to the tissue in the prostate. The rectal probe 34 has both a microwave element and an ultrasound element. A monitor 44 is electrically connected to the control system 20 for monitoring the procedure using ultrasound which is generated and received by the rectal probe 34.

Figure 2:
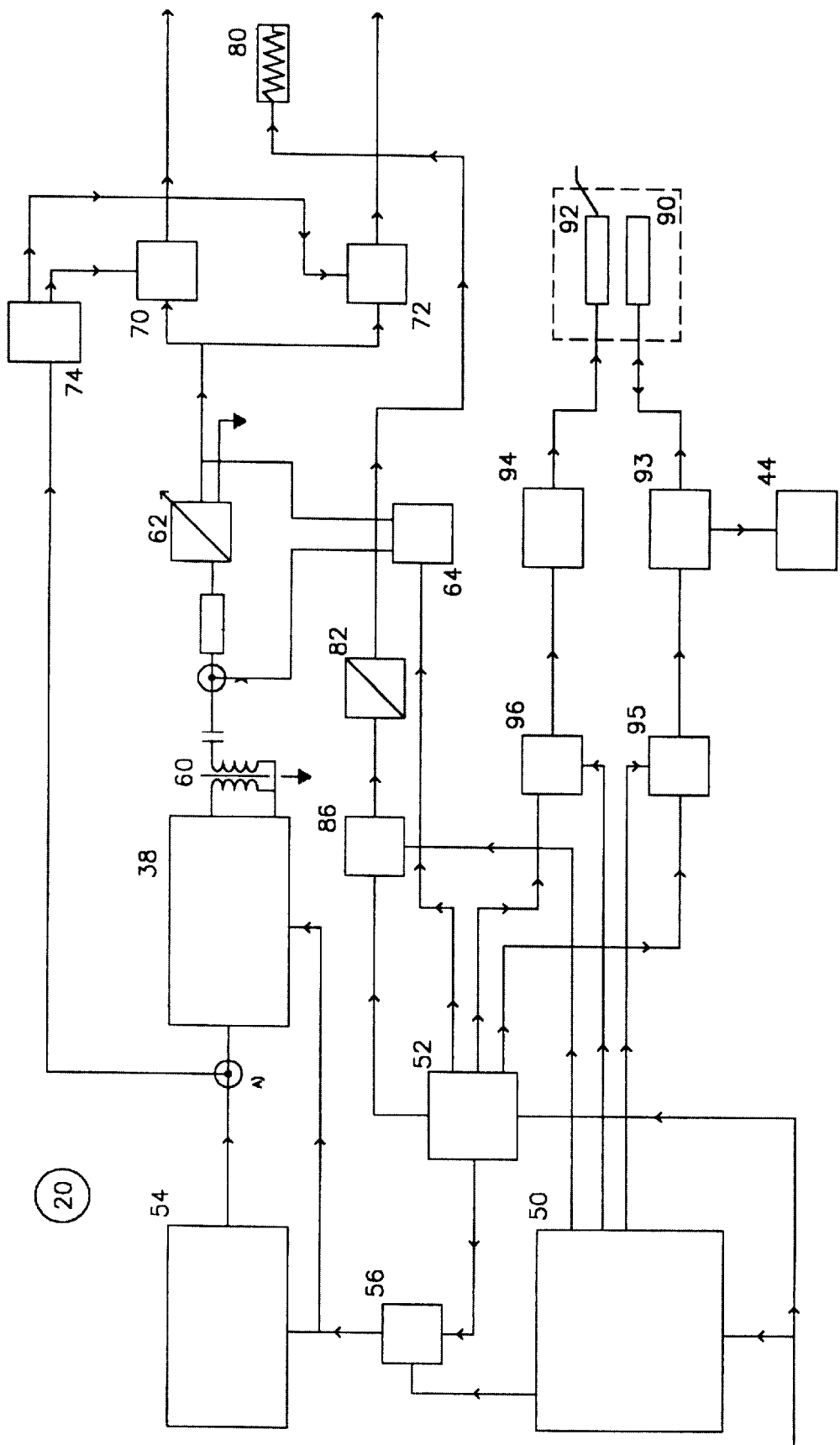
FIG. 2 is a block diagram of the control system of the present invention.

Referring particularly to FIG. 2, the control system 20 of the invention is shown in greater detail. A timing block 50 generates timing pulses for the system and a feeding block 52, which is directly connected to the AC power, allows for selective application of power to the various system components. The timing block 50 operates under program control to generate a plurality of timing pulses which are distributed to switching elements operatively connected to the various system components.

The urethral probe 34 is powered by a low frequency power source 54 which generates a 5 Hz square wave. The low frequency (LF) power source 54 is connected to the feeding block 52 via switch 56 which is controlled by timing block 50. The LF power source is connected to a 100 kHz multivibrator 58 which is connected to a transformer 60 which provides DC isolation. The output of the transformer 60 is connected through resistor R to a potentiometer 62 which is associated with adjustment means 26 and allows for operator control of the amplitude of the signal applied to two of the elements of the urethral probe 32 as will be explained later.

The transformer 60 is also connected to the display means 24 through display driver 64 for indicating the frequency and amplitude of the signal being applied to the urethral probe 32. An audible alarm may sound via speaker 28 in response to excessive amplitude or frequency as determined by display driver 64. The alarm levels may be set by the operator and may optionally be manually adjustable via control means attached to the housing. The display driver 64 is also connected to the feeding block so that the operator can be aware of the output levels thereof Display means 24 may be configured to display the status of the feeding block (e.g., on, off, low power, etc.). It should be noted here that display means 24 may be any combination of LEDs, LCDs, indicator lamps, or analog gauges.

The display driver 64 is connected to the output side of the potentiometer 62 to enable the operator to determine the voltage level of the signal applied to the patient. The signal from the potentiometer 62 is coupled to a pair of switches 70, 72 which are controlled by a triggering element 74 which is connected to receive the 5 Hz signal from the low frequency generator 54. The triggering element 74, which may be a flip flop or other logic element, alternately sends control signals to switches 70, 72 to allow for alternate energization of rings 76, 78 of the urethral probe 32 (FIG. 3) at a frequency of 2.5 Hz. The middle ring 80 of the urethral probe 32 is connected to the feeding block 52 through potentiometer 82 to produce low level heating. The amount of current supplied to, and therefore the amount heat generated by the middle ring 80 is limited by the switch 86 which is controlled by the timing block 50.

As has been previously stated, the rectal probe 34 has both an ultrasound element 90, and a microwave element 92. Power to the ultrasound element 90 is selectively applied from the feeding block 52 to the ultrasound generator 93 by switch 95 which is controlled by timing circuit 50. Power to the microwave element 92 is selectively applied from the feeding block 52 to the microwave generator 94 by switch 96 which is controlled by timing circuit 50. Reflected ultrasound is received by the ultrasound element 90 and fed back to the ultrasound generator 93 which includes circuitry for generating an image. The image signal is sent to monitor 44 so the operator can view the image.

Figure 3:
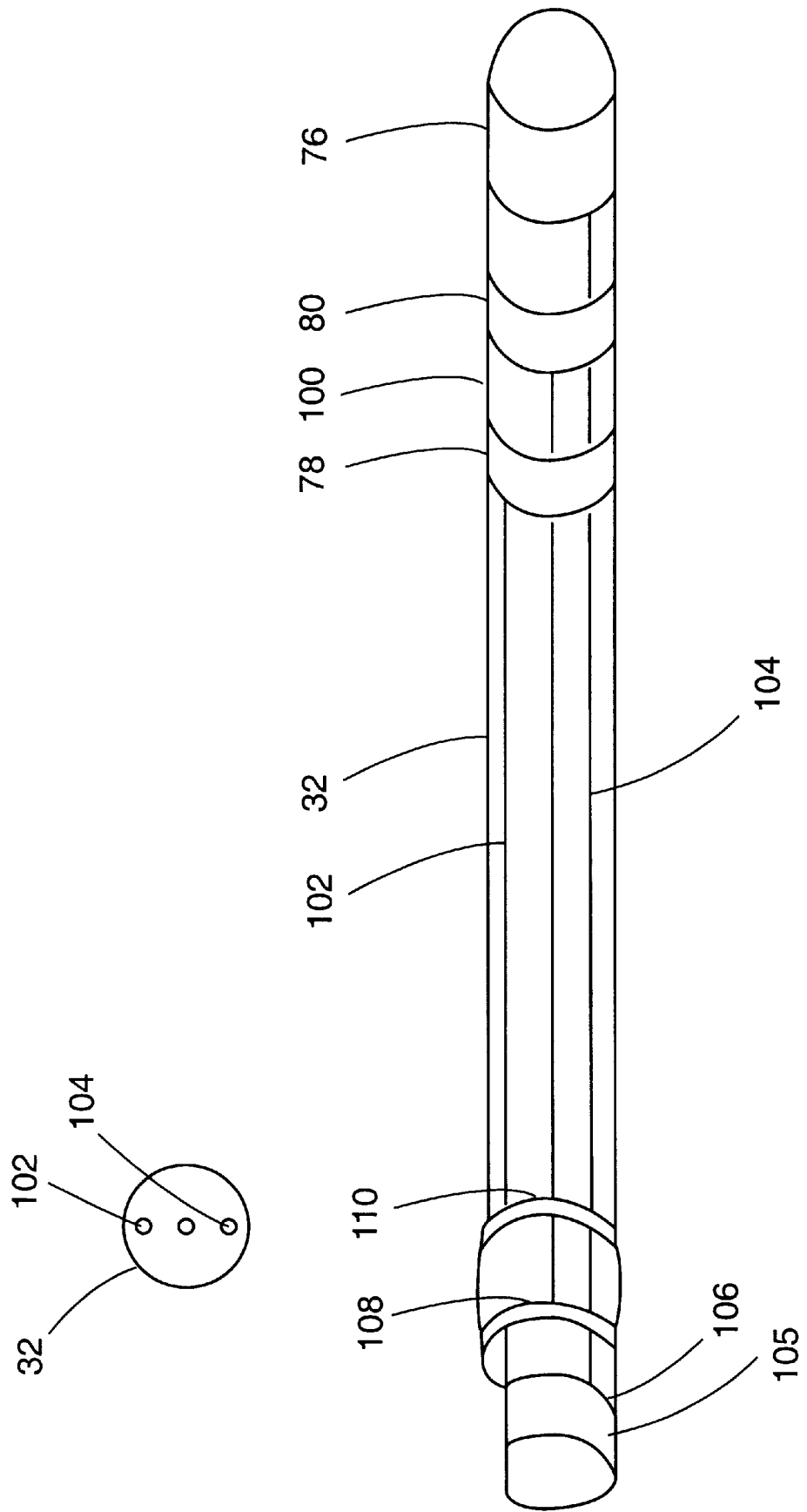
FIG. 3 is a isometric view partly in section of a urethral probe used with the present invention.
Figure 4:
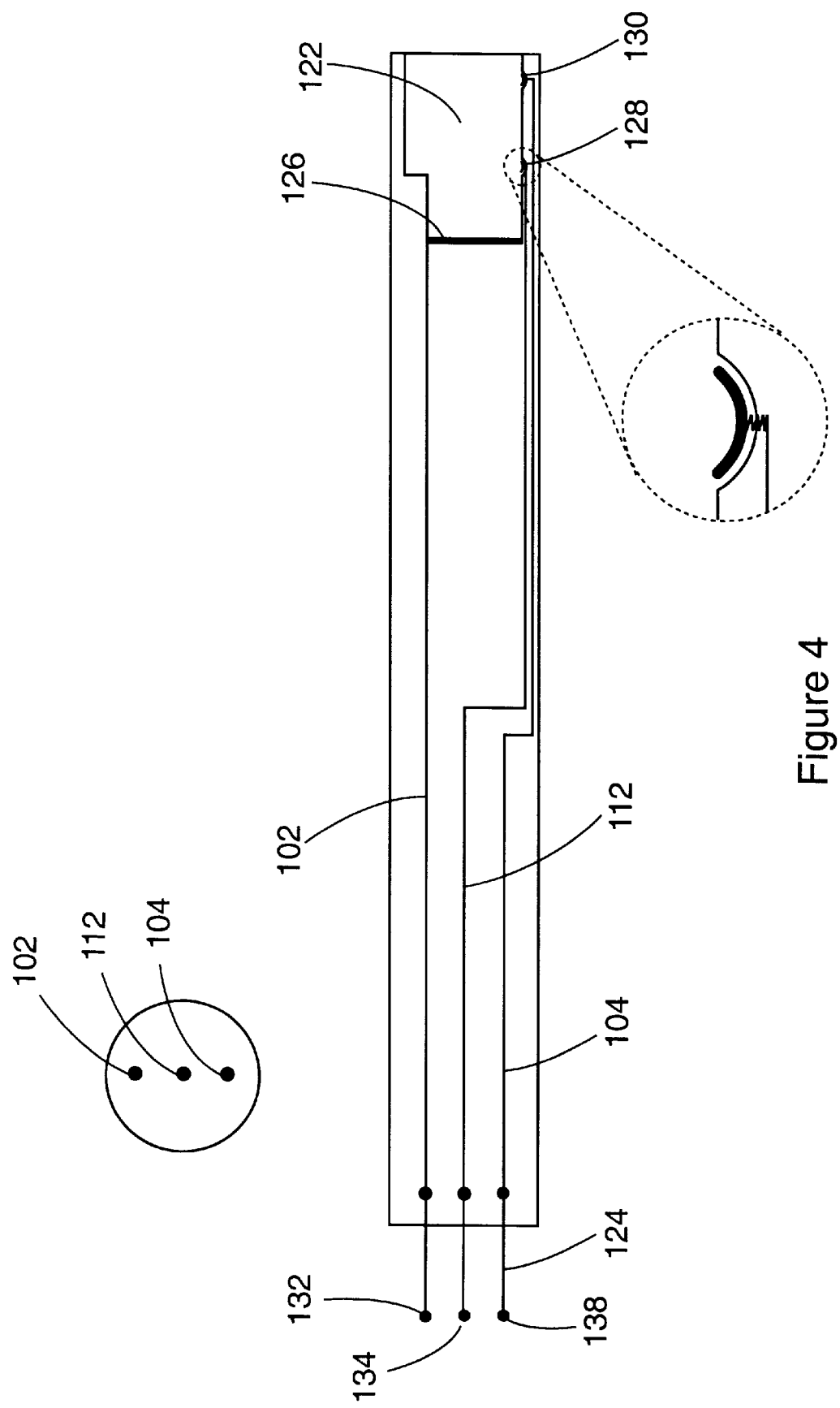
FIG. 4 is a plan view detailing the arrangement of conductors within the urethral probe.

Referring now particularly to FIGS. 3 and 4, details of the electrode structure and electrical connections of the urethral probe 32 are shown. The probe 32 has a distal end 100 with rings 76–80 as has been previously discussed. Rings 76 and 78 are connected to switches 70, 72 by wire pairs 102, 104 which are disposed interiorly of the casing of the probe 32. The distal end of the wire pairs 102, 104 are connected directly to the rings 76, 78 and the proximal or connecting end of the wire pairs 102, 104 is attached to a connector 105 having three electrically isolated conductive areas 106–110. Conductive areas 106 and 110 are connected to wire pairs 102 and 104. Conductive area 108 is connected to a third wire 112 which is connected at its distal end to middle ring 80. The connector 105 is connectable to a cable 120 having a socket 122 at one end and a pin arrangement 124 at the opposite end. Electrically isolated conductive areas 126–130 within the socket correspond to conductive areas 106–110, and pins 132, 134, and 136 are connected to wire pairs 138, 140, and 142 thereby allowing for connection of the rings 76–80 to the control circuit by insertion of the pin connector 124 into the terminal 36. The urethral probe 32 may be about 28 cm long and 12 mm in diameter and may be made out of clear plastic.

Figure 5:
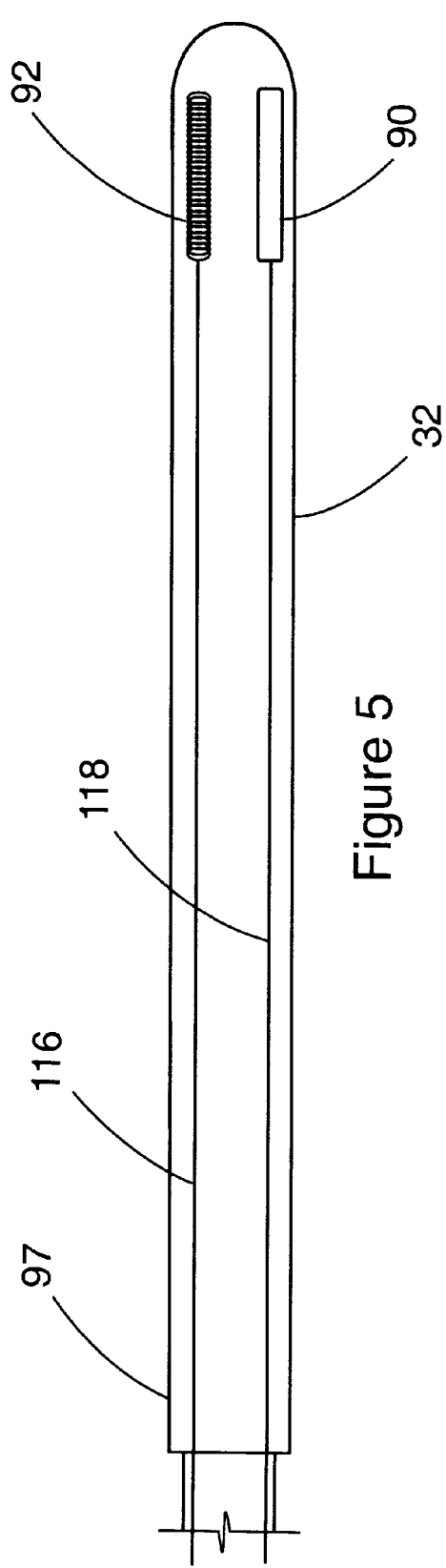
FIG. 5 is a side cross sectional view of a rectal probe used with the present invention.
Figure 6:
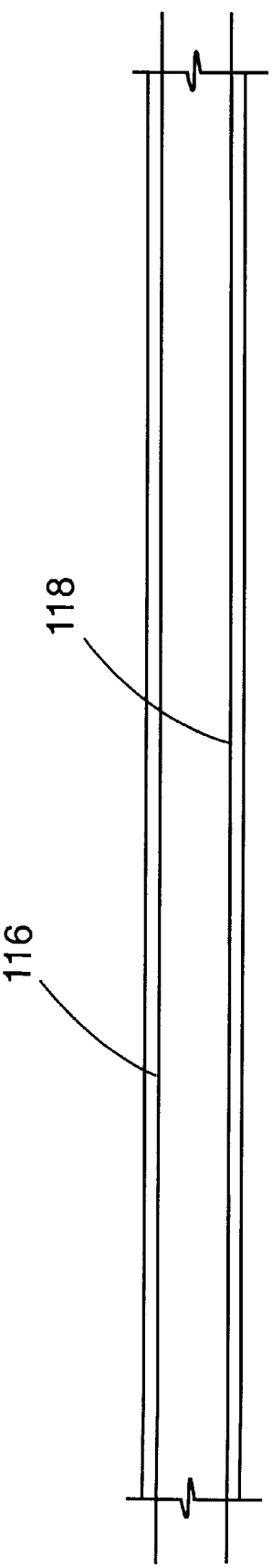
FIG. 6 is a plan view detailing the arrangement of conductors within the rectal probe.

Referring now to FIGS. 5 and 6, the details of the electrode structure and electrical connections for the rectal probe 32 are shown. The rectal probe 32 has the microwave element 92 and ultrasound element 90 mounted in fairly close proximity at the distal end of the probe 32. Conductors 116, 118 are connected between elements 90 and 92 and the respective generators 94 and 93. A suitable connector arrangement (not shown) may be used to connect wires 116, 118 to cable 150, which has conductors 152 and 154 disposed therein. The proximal end of the cable 150 is connected to terminal 38. The rectal probe 34 may be about 30 cm long and appropriately sized for insertion into the anal orifice. A plastic casing 97 may be used for the rectal probe 34.

Treatment of prostatitis is conducted by inserting the urethral probe 32 and the rectal probe 34 so that the array of active elements, 76–80, 90, and 92 are in close proximity to the tissues of the prostate and applying energy to the prostate area. Specifically, under local anesthesia Xylocain 2% jelly, the urethral probe 32 is inserted into the prostatic part of the urethra. From the tip of the probe 32, a 2.5 HZ low frequency signal is applied alternately to rings 76 and 78 for 15 minutes. The middle ring applies about 0.2 to 1 Watts of heat with care being taken not to apply excessive heat the area. The heat is applied for 5 minutes, with a 5 minute delay and then another 3 minute application.

The rectal probe 34 is inserted into the rectum through the anal orifice. From the microwave element, the patient is given 5–10 $\mu$a heat in order to increase the temperature in the surrounding tissue from 37.5–39 C. for 5 minutes, with a 5 minute delay and then another 3 minute application. The ultrasound element 90 generates a real time image signal which the operator may use to determine the condition of the surrounding tissue. Treatment may vary slightly from patient to patient depending upon effectiveness and patient feedback.

In all patients, the following effects were noted:

Inflammatory products, new or old, between the prostatic tissues, were removed from the prostate.

Increased prostatic blood circulation which enhanced antibacterial drug effect into the prostatic tissues.

Decreased the size of the inflamed prostate gland.

Eliminated the suprabic and perineal dull pain.

Eliminated the ejaculation pain.

Facilitated the micturation.

Enhanced, and in some cases restored erection.

Patients with a general tense condition due to the prostate problems, became more relaxed and productive in their work.

A yearly course of this method of treatment, can be prophilactic of BPH. After 6 to 10 procedures (full course of treatment), all treated patients become healthy.

The following clinical examples are illustrative of the effectiveness of the device.

Over 1250 patients with chronic prostatitis were treated. Patients were divided into four (4) groups:

1. The first group of 900 patients who were treated with the system 10 using the method of the invention.
   2 patients experienced less prostatic pain, but the burning sensation during urination continued.
   34 patients were treated for two (2) years using the device 10, and pain completely disappeared and rectal examination showed that the prostate was within normal range.
2. The second group having 200 patients who were treated by antibacterial (AB) medicine only. During this treatment, they felt well. However, when they stopped taking the antibacterial medicine, the clinical signs of prostatitis returned again.
3. Group three had 138 patients who delayed their treatment for 6 weeks. To decrease their pain, they were giving analgesics. However, the clinical signs of chronic prostatitis continued, as did the perineal and suprapubic dull pain.

4. Group four had 12 patients who have been treated by their doctors and given medication for neurogenic colone for 1–10 years. When their chronic prostatitis was diagnosed, they were treated by the device 10. 10 patients became healthy and stopped taking lexotanil, librax and other medication.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

I claim:

1. An apparatus for treating prostatitis comprising:

a urethral probe having a distal end and a proximal end, said distal end having a rounded, closed tip with a first electrode formed therein, a second electrode longitudinally spaced therefrom and electrically isolated therefrom, and a third electrode longitudinally spaced from said second and first electrodes and electrically isolated from said first and second electrodes, and said proximal end having a connector allowing for application of electrical power to said first, second, and third electrodes;

said first electrode covering the distal end, and said second electrode intermediate said first and third electrodes and having a heating element contained therein, said first and third electrodes adapted for receiving and generating heat from a low frequency source of alternating current power;

a rectal probe having a distal end and a proximal end, a microwave element and an ultrasound element mounted in said distal end, and;

control means connected to said urethral probe and said rectal probe for selectively applying power to said first, second, and third electrodes, and said microwave and ultrasound elements;

wherein said control means supplies power to said first, second, and third electrodes in accordance with a predetermined pattern.

2. The apparatus of claim 1 wherein said control means includes switching means operatively connected to a source of low frequency alternating current for alternately energizing said first and third electrodes.

3. A method of treating prostatitis in a patient having a prostate, a rectum, and a urethra comprising:

positioning a urethral probe in the urethra, said urethral probe having a distal end and a proximal end, said distal end positioned to effect treatment of said prostate and having three spaced electrodes for supplying energy to surrounding prostate tissue;

supplying a low frequency alternating current to a pair of said three electrodes, and supplying a heating current to a third of said three electrodes, said alternating current being a series of square wave pulses alternately supplied to said pair of electrodes;

positioning a rectal probe in said rectum, said rectal probe having a microwave element and an ultrasound element, said microwave element being positioned proximate said prostate tissue for supplying heat energy thereto;

intermittently energizing said microwave element to apply a controlled amount of heat to said prostate tissue.

4. The method of claim 3 wherein said pair of three electrodes are disposed on either side of said third electrode and wherein power is applied to said electrodes for about 5 minutes with a five minute delay before an application of power for three minutes.

5. The method of claim 3 wherein said microwave element is energized for about 5 minutes with a five minute delay before an application of power for three minutes.

6. The method of claim 5 wherein said microwave element is energized with sufficient power to bring the surrounding prostate tissue to a temperature of about 38 degrees centigrade.

* * * * *